(12) United States Patent
Li et al.

(10) Patent No.: US 7,751,985 B2
(45) Date of Patent: Jul. 6, 2010

(54) PROCESS FOR PREPARING SILK POLYPEPTIDE IN A CONTROLLABLE PARTICLE SIZE

(75) Inventors: Yi Li, Hung Hum (HK); Lok Yuen Lo, Hung Hum (HK); Jun Yan Hu, Hung Hum (HK)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 518 days.

(21) Appl. No.: 11/638,505

(22) Filed: Dec. 14, 2006

(65) Prior Publication Data

US 2008/0141792 A1 Jun. 19, 2008

(51) Int. Cl.
C07K 15/20 (2006.01)
C07K 15/00 (2006.01)
C07K 15/08 (2006.01)
G01N 33/50 (2006.01)

(52) U.S. Cl. .......................... 702/19; 530/353; 530/412; 530/422; 530/425; 702/29

(58) Field of Classification Search ........................ None
See application file for complete search history.

(56) References Cited

U.S. PATENT DOCUMENTS

| 4,233,211 | A | 11/1980 | Ohtomo et al. |
| 4,233,212 | A | 11/1980 | Otoi et al. |
| 5,718,954 | A | 2/1998 | Sano et al. |
| 5,853,764 | A | 12/1998 | Tsubouchi |
| 6,427,933 | B1 | 8/2002 | Tsubouchi |
| 7,115,388 | B2 | 10/2006 | Tsubouchi |

FOREIGN PATENT DOCUMENTS

WO WO 2005/085327 A1 9/2005

*Primary Examiner*—Michael Borin (57) ABSTRACT

The present invention relates to a process for controllably producing silk particles including the steps of designing a particle size, setting parameters to create the particle size except one unknown parameter, calculating the unknown parameter using algorithm, dissolving a silk peptide in a solvent, adding a cleavage agent, and hydrolyzing the peptide to produce the particle in the desired size.

18 Claims, 6 Drawing Sheets

Dissolution: 40° C for 50min C
Hydrolysis: 40° C for 60min C
Concentration of HCl: 3M

403

Dissolution: 40° C for 50min C
Hydrolysis: 80° C for 150min
Concentration of HCl: 6M

405

Dissolution: 80° C for 100min
Hydrolysis: 40° C for 60min
Concentration of HCl: 6M

402

Dissolution: 80° C for 100min
Hydrolysis: 80° C for 60min
Concentration of HCl: 3M

PROCESS FOR PREPARING SILK POLYPEPTIDE IN A CONTROLLABLE PARTICLE SIZE

BACKGROUND

Silk peptide is commonly applied as an additive to food, pharmaceuticals, and cosmetics. It has also become one of the most important components in paint and synthetic materials. The sense of toughness, the adhesion properties of cosmetics containing silk peptide to skin, the adhesion of paint coatings containing silk peptide, the thickness of synthesized structure, and the delivery or release properties of drugs are all affected by the particle size of silk peptide.

The particle size of silk peptide is generally affected by the preparation method. Mechanical comminuting obtains silk fibroin smaller than 3.0 µm and 10 µm. Pulverization of silk substances or regenerated silk fibroin gel collects particles either smaller than 1 µm, 3.0 µm, 10 µm, or between 15 and 30 µm. The combination application of centrifuge, filtering, and pulverization techniques produces powder in size 30-60 nm. However, all these techniques address the size of the particle after the particle has been made, requiring additional steps beyond producing the particle. Such additional require significant time and resources, and even still, the particles are not specific to one size or small range.

It is an object of the present system to overcome the disadvantages and problems in the prior art.

DETAILED DESCRIPTION

The present method relates to a process for controllably producing a silk particle.

The present method also relates to the use of an algorithm for designing and producing a silk particle of a desired particular size.

These and other features, aspects, and advantages of the apparatus and methods of the present invention will become better understood from the following description, appended claims, and accompanying drawings where:

The following description of certain embodiment(s) is exemplary in nature and is in not intended to limit the invention, its application, or uses. Throughout this description, the term "parameter" refers to a variable within a reaction that can be adjusted, modified, or manipulated.

The term "dissolution" refers to the process of a compound going into solution during a chemical reaction, such break up being capable of being brought about by heat, chemical reaction, and the like.

The term "dissolving" shall be used with reference to the process of dissolution.

The term "hydrolysis" shall refer to decomposition of a chemical compound by reaction with water.

The term "controllably" refers to the ability to design an object prior to production and to produce that object according to the specifications such forth in the design.

Figure 1:
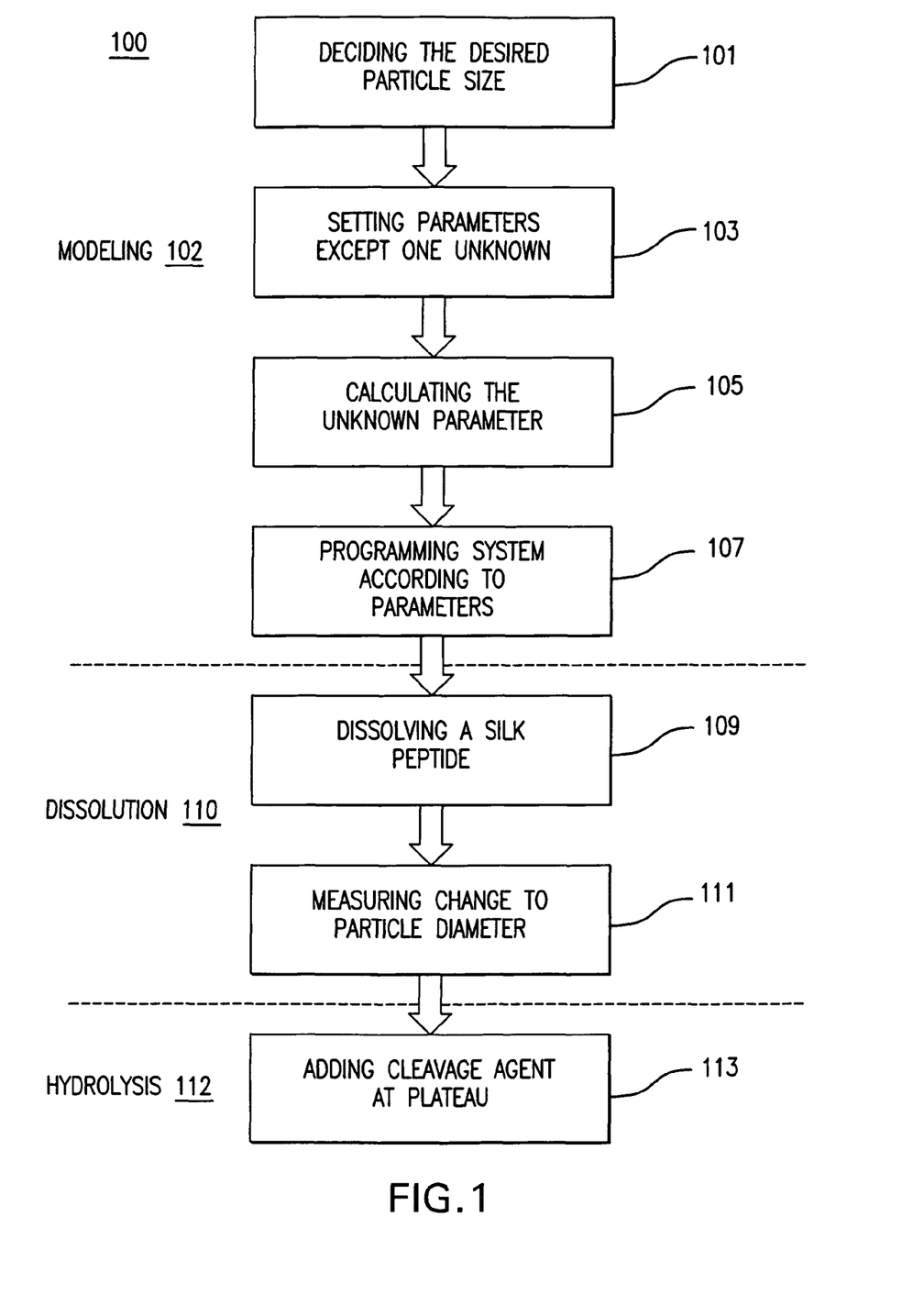
FIG. 1 shows an embodiment of the present method.

Now, specifically to embodiments shown in FIGS. 1-4,

FIG. 1 teaches an embodiment of the present method 100, consisting of three phases, wherein the first phase is modeling 102 whereby a desired particle size is decided upon 101, three parameters to be addressed when making the desired particle are set 103, a fourth parameter to be addressed when making the particle is calculated 105, and the system engaged to make the particle is programmed 107; in dissolution 110, the second phase, a silk peptide is dissolved within the system 109, and the unraveling silk peptide is measured 111; and during hydrolysis 112, the third phase, a cleaving agent is added to the solution 113, leading to the desired particle size.

During modeling 102, the desired particle size can be decided upon 101 based upon the future use of the silk particle. For example, WO 2005/085327 teaches the production of a silk particle in a size of from 30 to 60 nanometers for incorporation into various products. Desired particle size may also be decided based upon the desired properties of the resultant particles, such as conformation, aggregation potential, crystalline property, and the like. The desired particle size in the present method can be from 30 to 90 nm.

Setting the variable parameters 103 relates to consideration of the parameters that will lead to the desired particle size. The parameters in the present method can include the condition level during dissolution, the temperature during hydrolysis, duration of treatment during hydrolysis, and the concentration of the cleaving agent.

The condition level during dissolution refers to the severity of the conditions during dissolution 110. The condition level is a non-denominational number, i.e., does not contain a unit, and may be numbered from −1 to 1, with −1 being the least severe, and indicating that dissolution is decreased to such a level that it decreases the affect of the other parameters. As is shown in the present method, the severity of the condition affects the resultant particle size because it affects the degree of silk peptide chain extension (which occurs during dissolution 110). The higher the severity level, the larger the silk peptide chain extension. The severity of the dissolution 110 can be determined by the chemical properties of the starting material (silk peptide), the type of solvent used to dissolve the silk peptide, the concentration of solvent used to dissolve the silk peptide, the temperature at which dissolution occurs, and the length of time of dissolution.

Chemical properties of the silk peptide can relate to the different sources to obtain silk peptide, such as cocoons, raw silk, waste cocoons, raw silk waste, bisu, silk fabric waste, bourette, and the like. The silk peptide can include protein fibers, such as cocoon filaments, raw silk, silk fibers and knits, fibroin fiber, left over threads of the above or their ungummed material, half-degummed material, degummed material, fiber, power, and film. Characteristics pertaining to the different sources of the silk peptide are well known in the art.

As mentioned, the silk peptide may be degummed. Degumming is performed to remove sericin from the fibroin. Sericin is a silk protein composed of 4 components with a molecular weight of 40,000. As is well known in the art, an example of the degumming process involves boiling the silk peptide in an aqueous solution containing an alkaline sodium salt and soap. U.S. Pat. No. 7,115,388, incorporated herein by reference, teaches methods of degumming.

Types of solvents for use in dissolution of silk peptide include water, calcium nitrate, aqueous salt solutions containing alkali metal salt or alkaline earth metal salt, such alkali metal salts including LiCl, LiBr, NaI, $LiNO_3$, $MgCl_2$, $Mg(NO_3)_2$, $ZnCl_2$, $Zn(NO_3)_2$, LiSCN, NaSCN, $Ca(SCN)_2$, $Mg(SCN)_2$, $CaCl_2$, $Cu(NO_3)_2$, $Cu(NH_2CH_2CH_2NH_2)_2$, $CoH_2$, $Cu(NH_3)_4(OH)_2$, organic solvents as taught in U.S. Pat. No. 3,121,766, incorporated herein by reference, or combinations thereof in a molar ratio suitable for dissolving the silk fibroin.

The concentration of the solvent used to dissolve the silk peptide can also affect the severity during dissolution. The concentration of the solvent can be varied based upon the type of solvent, the type of solute, the temperature, and the like. In an example, in the case where the solvent is LiBr, and the silk fibroin is obtained from a raw silk thread, the concentration can be 7M. In another example, when the solvent is urea and the silk fibroin is obtained from silk containing sericin, the concentration can be 8M. For the present method, a concentration of from 1M to 8M can be used.

Dissolution can occur at various temperatures, ranging from 40° C. to 95° C. In one example, dissolution using urea to dissolve silk fibroin may occur between 70° C. and 90° C. In another example, lithium bromide is used to dissolve silk fibroin at a temperature of 45° C.

Dissolution is also a function of time, with the longer the length of time, the longer the silk chain can be extended. The length of time of dissolution 110 can occur between 10 minutes and 150 minutes. For example, dissolution occurs for 50 minutes at a temperature of 40° C. In another example, dissolution occurs for 100 minutes at a temperature of 80° C. In yet another example, dissolution occurs for 20 minutes at a temperature of 45° C.

Hydrolysis 112 techniques include an acid hydrolysis using hydrochloric acid, sulfuric acid, or the like, an alkali hydrolysis using sodium hydroxide, sodium carbonate, or the like, and an enzyme hydrolysis using protease. U.S. Pat. Nos. 4,839,168 and 5,009,813, incorporated herein by reference, teach suitable methods of hydrolysis.

In the present process, hydrolysis 112 can occur between temperatures of 20° C. and 95° C. For example, hydrolyzing with HCl can occur at 40° C. In another example, hydrolyzing with HCl can occur at 80° C.

Duration or time of treatment during hydrolysis 112 can be in accordance with known methods of hydrolysis. A duration range of between 60 minutes to 150 minutes is suitable. In one example, hydrolysis with HCl occurs for 100 minutes. In another example, hydrolysis with HCl occurs for 150 minutes.

Concentration of the cleaving agent can be from 3M to 6M, however a higher molar can be used, if required, based upon the specific cleaving agent. Suitable cleaving agents can include enzymes, hydroxylamine, and a dilute acid, for example, lysyl endopeptidase, serine protease, metalloendopeptidase, arginyl endopeptidase, metalloprotease, chymotrypsin, papain, Alcalase, pepsin, rennin, pancreatin, elastase, carboxypeptidase, aminopeptidase, dipeptidase, and the like. Chemicals used in chemical cleavage method include cyanogens bromide, N-bromosuccinimide, BNPS-scatol (2-(2-nitrophenylsulfenyl)-3-methyl-3-bromoindole), dimethylsulfoxide, O-iodosobenzoic acid, hydroxylamine, dilute acid, and the like.

In setting the parameters 103 during modeling 102, all parameters are set except one. In this method, the resultant particle size is controlled by manipulating the last parameter. For example, during modeling 102, the desired particle size is decided upon, and the temperature during hydrolysis, the duration of treatment during hydrolysis, and the concentration of the cleaving agent are set. By inserting the known parameters and desired resultant particle size into an algorithm made in accordance with the present method, the condition level of dissolution can be determined. During dissolution, the condition level is manipulated such that it conforms to the determined condition level, thus resulting in the desired particle size. Any of the parameters may be set, and likewise any one of the parameters may be left unset, to be determined utilizing the algorithm. In one embodiment, the condition level during dissolution is left unknown.

Calculating the unknown parameter 105, as stated above, relates to determining the parameter that will be manipulated to provide the desired particle size. Calculating will involve inserting the set parameters and desired particle size into an algorithm developed in accordance with the present process, such algorithm being, $$y=C_0+C_1x_1+C_2x_2+C_3x_3+C_4x_4+C_{12}x_1x_2+C_{13}x_1x_3+\\C_{14}x_1x_4+C_{23}x_2x_3+C_{24}x_2x_4+C_{34}x_3x_4+C_{123}x_1x_2x_3+\\C_{124}x_1x_2x_4+C_{134}x_1x_3x_4+C_{234}x_2x_3x_4+\\C_{1234}x_1x_2x_3x_4$$

where,
 y=particle size
 $x_1$=condition level of dissolution
 $x_2$=hydrolysis temperature
 $x_3$=hydrolysis duration
 $x_4$=concentration of cleaving agent

| | |
|---|---|
| C0 = | 67.542 |
| C1 = | 2.458 |
| C2 = | 0.625 |
| C3 = | 1.792 |
| C4 = | 3.750 |
| C12 = | −5.375 |
| C13 = | 1.542 |
| C14 = | −2.000 |
| C23 = | 1.625 |
| C24 = | 4.500 |
| C34 = | −1.500 |
| C123 = | −4.708 |
| C124 = | 5.167 |
| C134 = | 4.917 |
| C234 = | −1.167 |
| C1234 = | −1.167 |

Calculation of the unknown parameter 105 can occur manually or automatically. The algorithm may be stored on the memory of a computer system, such computer system comprising a display, user interface, processor, and storage means, such as a memory, and other necessary implements for operation. The computer system can be a laptop, tabletop, or handheld, such as PDA. In a further embodiment, the algorithm can be used to calculate a range for the parameter to operate within in order to obtain a resultant particle range. For example, if it is desired to obtain a particle with a range of 60 to 70 nm, the algorithm is useful for determining the range in which the unset parameter must be set. In one example, the unknown parameter may be $x_1$, wherein the set parameters are $x_2$, $x_3$, and $x_4$, and the y is the desired particle size.

Programming the system with the parameters 107 to deliver the desired particle size involves setting the condition level, such as the concentration of solvent, temperature of solvent, selecting the source of silk fibroin, etc., setting the processing temperature during hydrolyzation, setting the duration of treatment with the cleavage agent, or creating a cleavage agent solution in the appropriate concentration. In programming the system, all of the parameters are programmed, with the previously unset parameter being manipulated to ensure a desired particle size.

During dissolution 110, the making of the particle is initiated. A silk peptide is firstly dissolved in a solvent in such conditions as previously described. Prior to dissolving, the silk peptide may be treated by methods such as washing, drying, degumming, and the like. Dissolution 110 will occur for a set period of time at a set condition level. Dissolution 110 can continue until the silk peptide has unraveled to its fullest extent and reached plateau. In another embodiment, dissolution 110 can discontinue at a point before the silk peptide reaching its fullest unraveling extent. In determining the size of the silk peptide as its unravels, the particle size in solution can continually be measured 111.

Measurement 111 can occur in accordance with ISO-13320-1 (Particle size analysis-laser diffraction methods) standards, using a laser particle size analyzer. In another embodiment, other techniques may be used such as visualization of nanoscale particles in liquids on an individual basis as performed by the Halo LM10™ (NanoSight). Measurement can be performed in real time in order to determine the point at which the silk peptide extension has reached plateau.

Following the plateau of particle size growth, a cleaving agent, as previously mentioned, or other energy source is added to the solution to cleave the bonds of the silk peptide chain. In one embodiment, HCl is added as the cleaving agent. Other energy sources can include light, heat, radiation, and the like.

In another embodiment, the cleaving agent is added to the solution prior to the particle size growth reaching plateau. In this embodiment, cleaved silk peptide chain is still in a coiled state but small diameter.

Following cleavage, the silk particles are allowed to contract to a particular diameter, at which point they stabilize or level off. The point of leveling off of the silk particle contraction can be determined by measuring in accordance with ISO-13320-1 standards.

The particle are now prepared for inclusion in various products, such as films, powders, gels, cosmetics, and the like. Other substances that may be present in the resultant solution can be removed by techniques such as desalting and the like.

In another embodiment, as will be discussed later, 3 embodiments may be used in the process for controlling silk particle size.

Figure 2:
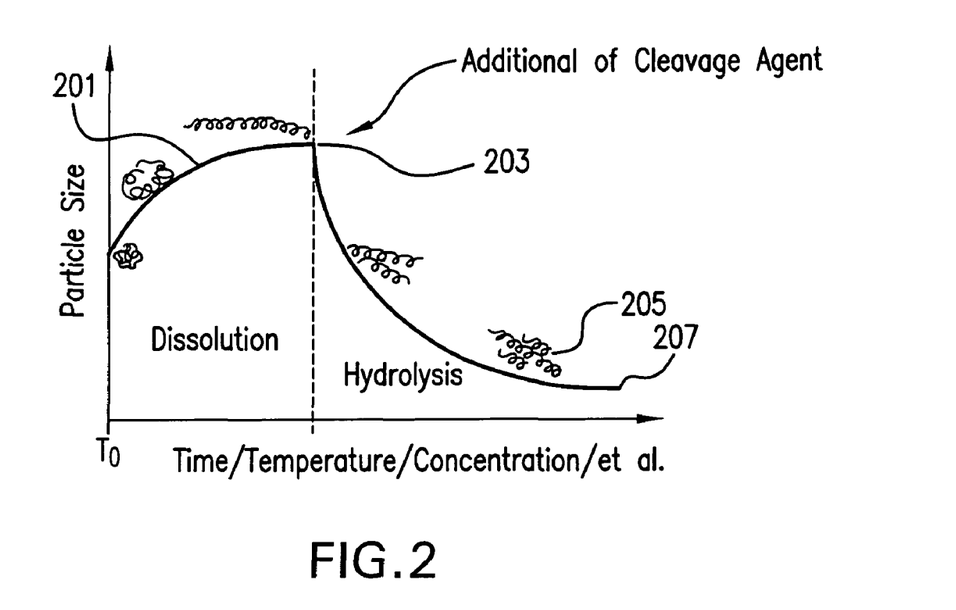
FIG. 2 shows progression of the production of a particle in accordance with the present method.

FIG. 2 is a graphical representation of the affect of the present process, wherein particle size is a function of duration of the reaction, temperature of solution, concentration of solution, and the like. As shown in FIG. 2, the silk peptide starting at $T_o$ unravels during dissolution 201 to a point at which the silk peptide chain is at its fullest extent and has reached plateau. At a time after plateau, a cleaving agent is added 203 to the solution to split the peptide chain into smaller units. The smaller units are then hydrolyzed 205. As shown by FIG. 2, the silk particle size contracts until it levels off 207. A time after leveling off is the point at which the particle is at the desired size. The present method has as its goal the control of the resultant particle size by controlling one of the parameters involved in making silk particles. The control of the parameter is brought about by calculating the parameter's amount using the algorithm as taught by the present method, and then applying that amount the system. In one embodiment, the controlled parameter is the condition level during dissolution. The higher the severity of condition level during dissolution, the more the peptide chain is extended during dissolution. Following hydrolysis, this results in a smaller particle size.

Figure 3:
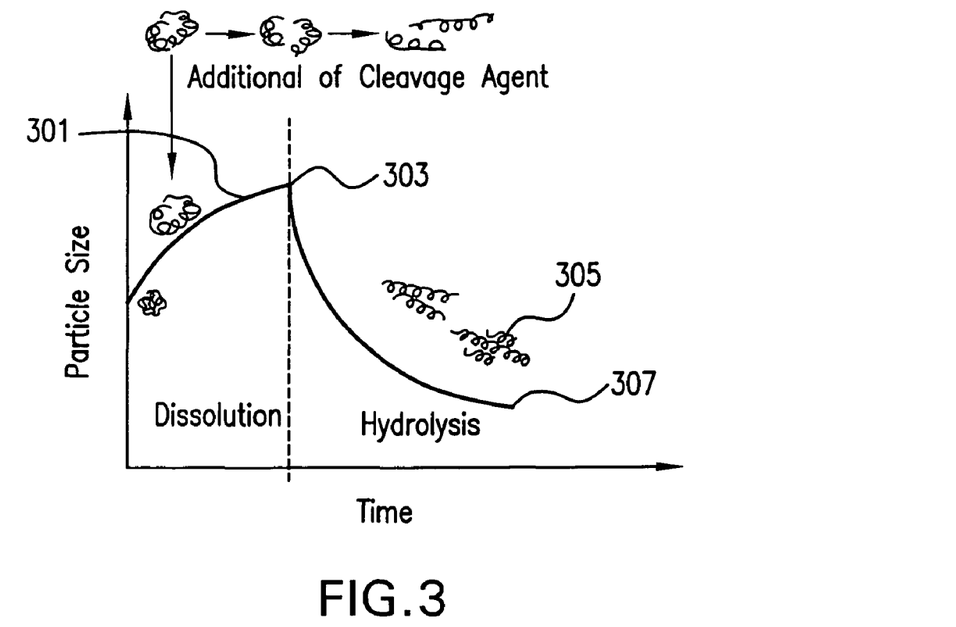
FIG. 3 shows an embodiment of progression of the production of a particle in accordance with the present method.

FIG. 3 is an embodiment of the present process comprising dissolution 301, a cleavage point 303, and a hydrolysis 305. In this embodiment, particle size is a function of time. A peptide with a higher molecular weight within a small particle size, when compared with the embodiment in FIG. 2, is obtained by cleaving the silk peptide before it plateaus.

EXAMPLE

A silk particle size of 52 nm, was decided upon. Following setting the hydrolysis temperature at 40° C., the duration of hydrolysis at 60 minutes, and the concentration of the cleavage agent, HCL, at 3M, the condition level of the dissolution was manually calculated using the below algorithm;

$$y = C_0 C_1 x_1 + C_2 x_2 + C_3 x_3 + C_4 x_4 + C_{12} x_1 x_2 + C_{13} x_1 x_3 + C_{14} x_1 x_4 + C_{23} x_2 x_3 + C_{24} x_2 x_4 + C_{34} x_3 x_4 + C_{123} x_1 x_2 x_3 + C_{124} x_1 x_2 x_4 + C_{134} x_1 x_3 x_4 + C_{234} x_2 x_3 x_4 + C_{1234} x_1 x_2 x_3 x_4$$

where the various variables were as previously disclosed. The experiment was then run where 10 g of silk powder NS001 produced by Nano-Sports Technologies Limited was dissolved in 100 g mixture of calcium chloride, water, and ethanol in a mole ratio of 1:8:2. The solution was allowed to progress until it was determined by laser particle size analysis that the growth particle size had reached plateau. Following, HCl was added, and hydrolysis followed.

Figure 4:
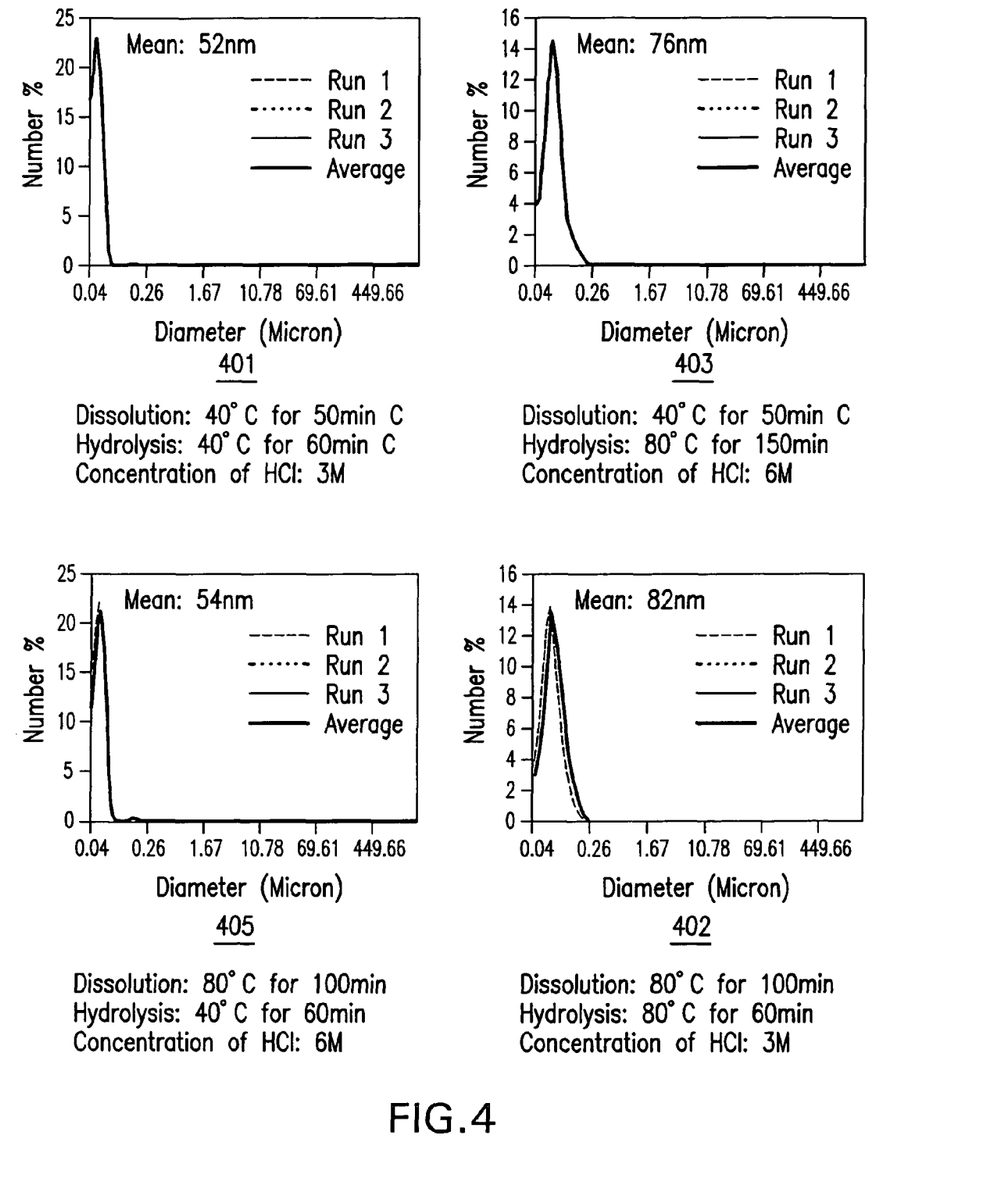
FIG. 4 shows examples according to the present method.

As shown in FIG. 4, After determining the contracting particle size had leveled off, as determined by laser analysis, a final measurement was taken to ensure the resultant particle size had been achieved 401.

Further to FIG. 4, the process was applied to more examples, such as for a desired particle size of 76 nm 403, a desired particle size of 54 nm 405, and a desired particle size of 82 nm 407.

Figure 5:
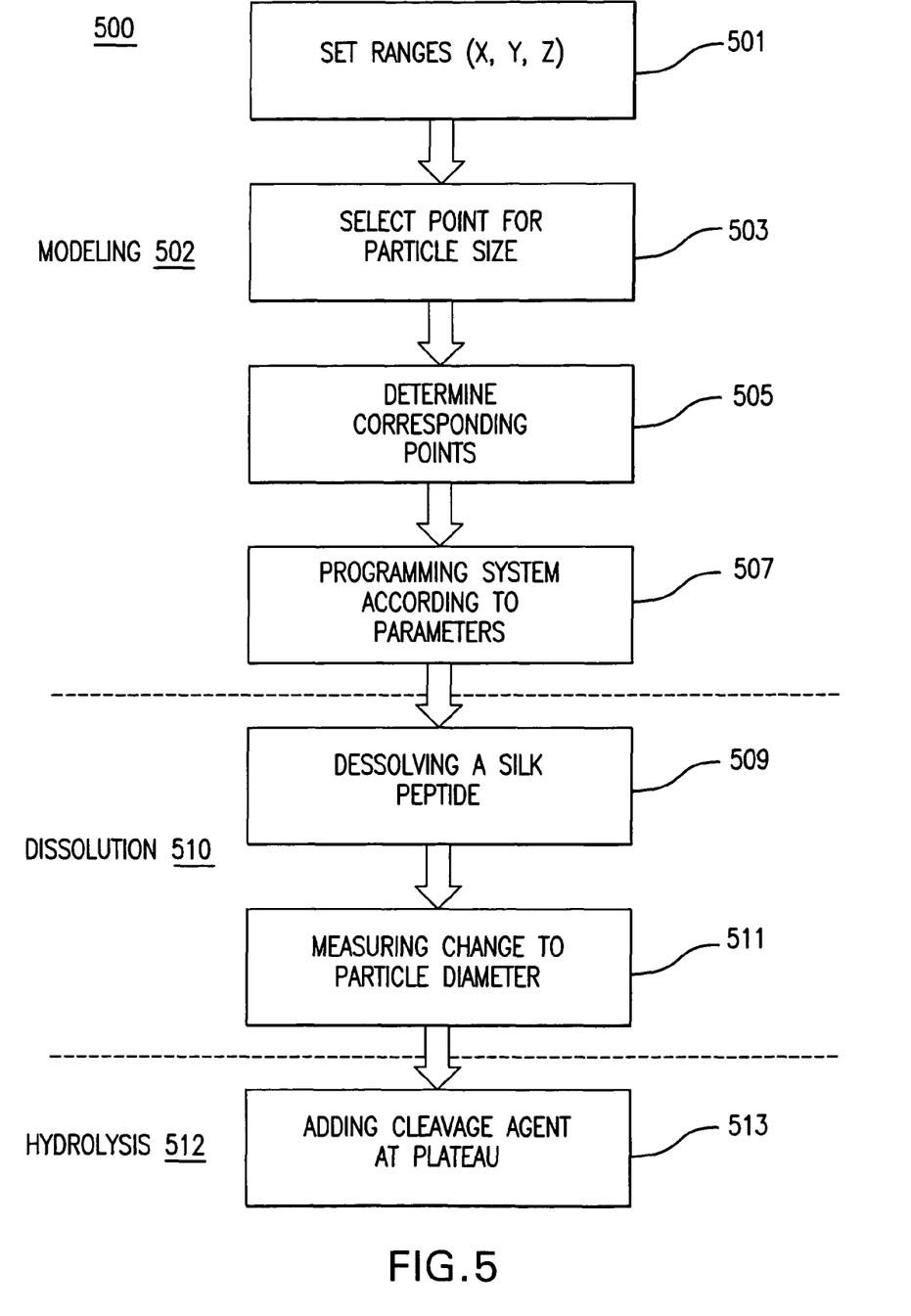
FIG. 5 shows another embodiment of the present invention, involving the use of three phases to make the desired particle size.

FIG. 5 is another embodiment of the present method, wherein in three phases a particle of desired sized can be made 500. The first phase is modeling 502, the second phase is dissolution 510, and the third phase is hydrolysis 512.

During modeling 502, as discussed the desired particle size can be decided upon based upon the future use of the silk particle. The desired particle size in the present method can be from 30 to 90 nm. In this embodiment, ranges are set for three parameters, and then plotted on a three-dimensional graph. For example, a range can be set for particle size of between 30 to 90 nm, the concentration of cleaving agent of between 3M and 6M, and the level of dissolution of between −1 and 1. In another example, ranges can be set for particle size of between 30 to 90 nm, the temperature during hydrolysis of between 40° C. and 80° C., and the temperature during hydrolysis of between 50° C. and 150° C. As stated, the ranges are then placed on a three dimensional graph, for example particle size can be set on the x-axis, concentration of cleaving agent can be set on the y-axis, and level of dissolution can be set on the z-axis. In another embodiment, the particle size can be placed on the x-axis, the time for hydrolysis can be placed on the y-axis, and the temperature during hydrolysis can be placed on the z-axis.

Following setting the ranges 501, a particle size can be selected and positioned on the graph 503.

Following, the positioning of the particle size on the graph 503 will allow determination of the corresponding y and z points 503. The determination of the corresponding y and z points will correspond to the specific parameters necessary to bring about the particle size. For example, if particle size is set, a user is now able to determine the concentration of cleaving agent, and level of dissolution necessary to bring about the desired particle size. Likewise, setting of the particle size will allow determination of the temperature and time of hydrolysis.

The system may now be programmed with the determined parameters for the production of a silk particle in the desired size 507.

During dissolution 510, as detailed previously, the making of the particle is initiated, whereby the silk peptide is dissolved in solution 509. Measurements can occur to observe the change in diameter of the silk peptide.

As previously detailed, hydrolysis 512 occurs following the addition of the cleaving agent.

Figure 6:
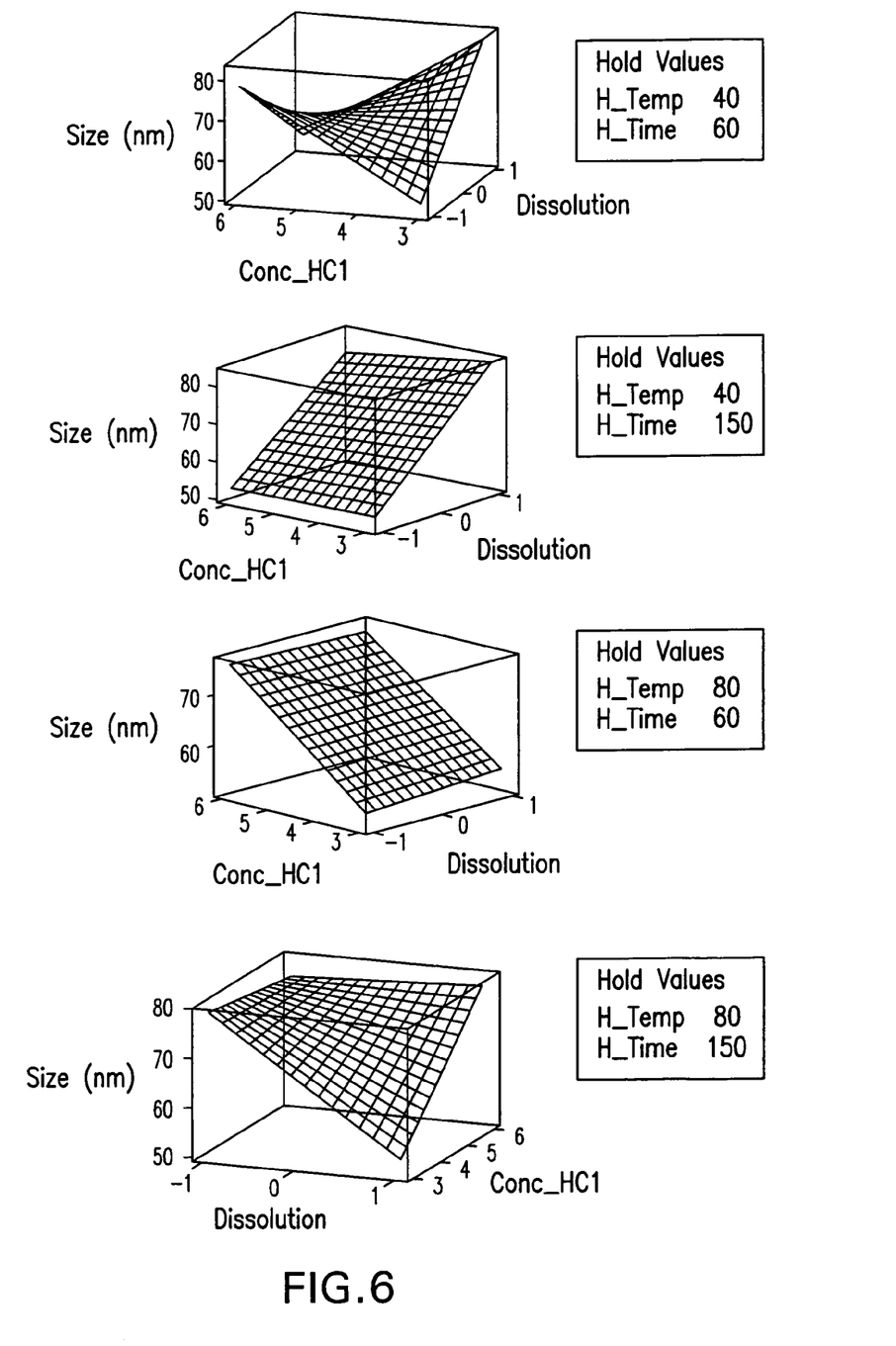
FIG. 6 shows modeling to determine the parameters required to make the desired particle size are positioned on a three-dimensional graph.

FIG. 6 shows an embodiment of the present method, whereby modeling to determine the parameters required to make the desired particle size are positioned on a three-dimensional graph. The parameters are concentration of cleaving agent (HCl) (y-axis), and dissolution level (z-axis).

Figure 7:
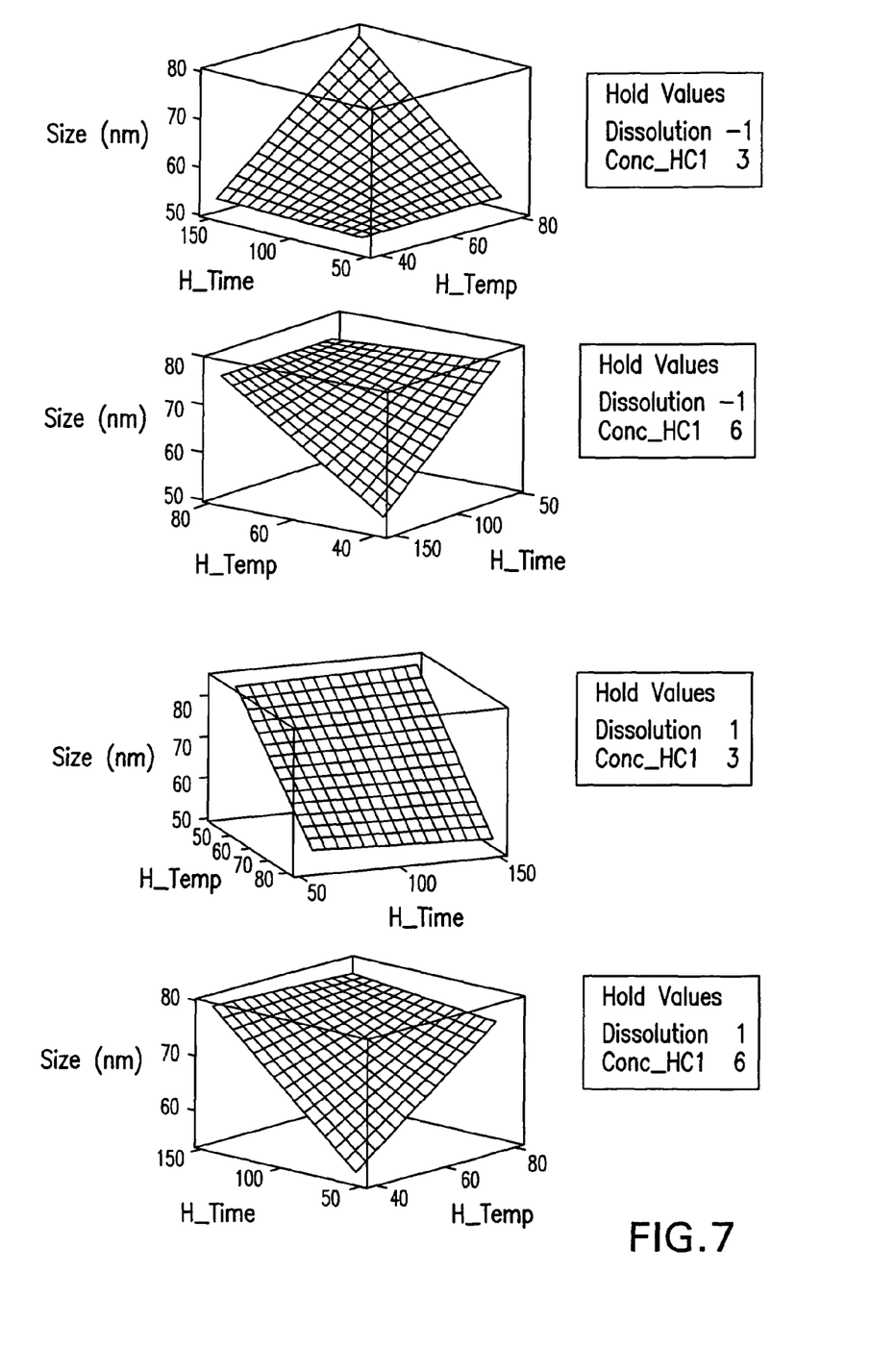
FIG. 7 shows a further embodiment of the present method, whereby modeling to determine the parameters required to make the desired particle size are positioned on a three-dimensional graph.

FIG. 7 shows a further embodiment of the present method, whereby modeling to determine the parameters required to make the desired particle size are positioned on a three-dimensional graph. The parameters are hydrolysis time (y-axis), and temperature during hydrolysis (z-axis).

Having described embodiments of the present system with reference to the accompanying drawings, should be understood that the present system and the methods, are not limited to the precise embodiments, and that various changes and modifications may be effected therein by one having ordinary skill in the art without departing from the scope or spirit as defined in the appended claims.

In interpreting the appended claims, it should be understood that:

a) the word "comprising" does not exclude the presence of other elements or acts than those listed in the given claim;

b) the word "a" or "an" preceding an element does not exclude the presence of a plurality of such elements;

c) any reference signs in the claims do not limit their scope;

d) any of the disclosed devices or portions thereof may be combined together or separated into further portions unless specifically stated otherwise; and e) no specific sequence of acts or steps is intended to be required unless specifically indicated.

The invention claimed is:

1. A process for controllably producing silk particles comprising, deciding a desired particle size;

setting parameters relating to production of said particles except an unknown parameter;

calculating said unknown parameter using the algorithm $$y = C_0 + C_1 x_1 + C_2 x_2 + C_3 x_3 + C_4 x_4 + C_{12} x_1 x_2 + C_{13} x_1 x_3 + C_{14} x_1 x_4 + C_{23} x_2 x_3 + C_{24} x_2 x_4 + C_{34} x_3 x_4 + C_{123} x_1 x_2 x_3 + C_{124} x_1 x_2 x_4 + C_{134} x_1 x_3 x_4 + C_{234} x_2 x_3 x_4 + C_{1234} x_1 x_2 x_3 x_4$$

where, $y$ = particle size in nanometer
$x_1$ = condition level of dissolution (from −1 to 1)
$x_2$ = hydrolysis temperature in degree Celsius
$x_3$ = hydrolysis duration in Minutes
$x_4$ = concentration of cleaving agent in Molar C0 = 67.542
C1 = 2.458
C2 = 0.625
C3 = 1.792
C4 = 3.750
C12 = −5.375
C13 = 1.542
C14 = −2.000
C23 = 1.625
C24 = 4.500
C34 = −1.500
C123 = −4.708
C124 = 5.167
C134 = 4.917
C234 = −1.167
C1234 = −1.167;

programming a system to produce said silk particles;
dissolving silk protein powders in a solvent to form a solution;
adding a cleaving agent to the solution;
hydrolyzing said silk protein powders; and
measuring said silk protein powders.

2. The process in claim 1, wherein said desired particle size is between 30 to 90 nm.

3. The process in claim 1, wherein said parameters include condition level of dissolution, temperature during hydrolysis, duration of hydrolysis, and concentration of said cleaving agent.

4. The process in claim 3, wherein said condition level can be numbered from −1 to 1, where −1 is the least severe level.

5. The process in claim 4, wherein said condition level is determined by the chemical properties of said silk protein powders, said solvent used to dissolve said silk protein powders, the concentration of said solvent, the temperature during dissolution, and the duration of dissolution.

6. The process in claim 5, wherein said silk protein powders is derived from cocoons, raw silk, waste cocoons, raw silk, waste, bisu, silk fabric waste, or bourette.

7. The process in claim 5, wherein said solvent is selected from the group consisting of water, aqueous salt solutions, organic solvents, alcohols, or a combination thereof.

8. The process in claim 5, wherein the temperature during dissolution is from 40° C. to 95° C.

9. The process in claim 5, wherein the duration of time during dissolution is from 10 to 150 minutes.

10. The process in claim 3, wherein temperature during hydrolysis can be from 20° C. to 95° C.

11. The process in claim 3, wherein duration of hydrolysis is from 60 minutes to 150 minutes.

12. The process in claim 3, wherein the concentration of said cleaving agent can be from 3M to 6M.

13. The process of claim 1, wherein said unknown parameter is the condition level of dissolution.

14. The process of claim 1, wherein dissolving said silk protein powders occurs in a condition commensurate with calculated condition level.

15. The process of claim 1, wherein measuring said silk protein powders includes using laser particle size analysis.

16. The process of claim 1, wherein said cleaving agent is added when said dissoluting silk protein powders plateaus.

17. The process of claim 1, wherein said cleaving agent is added prior to the dissoluting silk protein powders plateaus.

18. The process of claim 1, wherein said cleaving agent is HCl.

* * * * *